(12) United States Patent
Schiemann et al.

(10) Patent No.: US 6,794,139 B2
(45) Date of Patent: Sep. 21, 2004

(54) BREAST CARCINOMA-ASSOCIATED GENE

(75) Inventors: Sabine Schiemann, Kaiserslautern (DE); Ulrich Weidle, München (DE)

(73) Assignee: Roche Diagnostics GmbH, Mannheim (DE)

(*) Notice: Subject to any disclaimer, the term of this patent is extended or adjusted under 35 U.S.C. 154(b) by 0 days.

(21) Appl. No.: 09/999,699

(22) Filed: Oct. 24, 2001

(65) Prior Publication Data

US 2002/0127579 A1 Sep. 12, 2002

Related U.S. Application Data

(63) Continuation of application No. 09/254,129, filed on May 12, 1999.

(30) Foreign Application Priority Data

Sep. 3, 1996 (EP) .............................. 96114098
Sep. 2, 1997 (WO) ............................... PCT/EP97/04785

(51) Int. Cl.[7] .......................... C12Q 1/68; C07H 21/02; C07H 21/04
(52) U.S. Cl. ........................... 435/6; 536/23.1; 536/24.3
(58) Field of Search .............................. 435/6; 536/23.1, 536/24.3

(56) References Cited

U.S. PATENT DOCUMENTS 5,882,864 A    3/1999   An et al.

FOREIGN PATENT DOCUMENTS

WO    WO 97/19171    5/1997

OTHER PUBLICATIONS

Gnirke et al., "Investigation of Prevalence and Regulation of Expression of Progression Associated Protein (PAP)", Anticancer Res., vol. 18, p. 4363–4370 (1998).*

Poste, G., "Experimental systems for analysis of the malignant phenotype", Cancer Metastasis Reviews, vol. 1, pp. 141–199 (1982).*

GeneBank Accession No. HSB4BMR, H. sapiens mRNA for B4B, Jul. 24, 1996.*

Marvin, et al, Identification and Characterization of Novel Squamous Cell–associated Gene Related to PMP22*, The Journal of Biological Chemistry, vol. 270, No. 48, pp. 28910–28916 (1995).

Ruegg, et al., B4B, a Novel Growth–Arrest Gene, Is Expressed by a Subset of Progenitor/Pre–B Lymphocytes Negative for Cytoplasmic $\mu$–Chain[1], Journal of Immunology, vol. 157, pp. 72–80 (1996).

Schiemann, et al., Differential Gene Expression in Human Mammary Carcinoma Cells: Identification of a New Member of a Receptor Family, Anticancer Research, vol. 17, pp. 13–30 (1997).

Taylor, et al., J. Biol. Chem. 270 (1995) pp. 28824–28833.

Hayasaka, et al., BBRC (1992) vol. 186, No. 2, pp. 827–831.

Edomi, P., Gene, 126 (1993), pp. 289–290.

Welcher, et al. Proc. Nat'l. Acad. Sci. USA 88 (1991) pp. 7195–7199.

Spreyer, et al., EMBO, J. 10 (1991) pp. 3661–3668.

Stein, A. & Cheng, Y. Antisense Oligonucleotides as Therapeutic Agents . . . Science 261, pp. 1004–1012 (1993).

Dermer, G.B., Another Anniversary for the War on Cancer, Biotechnology, pp. 12:320, (1994).

* cited by examiner

*Primary Examiner*—Jeffrey Fredman
*Assistant Examiner*—Teresa Strzelecka
(74) *Attorney, Agent, or Firm*—George W. Johnston; Patricia S. Rocha-Tramaloni

(57) ABSTRACT

A pharmaceutical composition is disclosed, as well as its use in tumour diagnosis, therapy and prevention, methods for diagnosing, treating and preventing tumours, and antibodies and their use.

2 Claims, 2 Drawing Sheets

SEQUENCE LISTING

<160> NUMBER OF SEQ ID NOS: 10

<210> SEQ ID NO 1
<211> LENGTH: 2786
<212> TYPE: DNA
<213> ORGANISM: Homo sapiens
<220> FEATURE:
<221> NAME/KEY: CDS
<222> LOCATION: (219)..(689)

<400> SEQUENCE: 1

```
agcactctcc agcctctcac cgcaaaatta cacaccccag tacaccagca gaggaaactt    60
ataacctcgg gaggcgggtc cttcccctca gtgcggtcac atacttccag aagagcggac   120
cagggctgct gccagcacct gccactcaga gcgcctctgt cgctgggacc cttcagaact   180
ctctttgctc acaagttacc aaaaaaaaaa gagccaac atg ttg gta ttg ctg gct   236
                                          Met Leu Val Leu Leu Ala
                                            1               5 ggt atc ttt gtg gtc cac atc gct act gtt att atg cta ttt gtt agc    284
Gly Ile Phe Val Val His Ile Ala Thr Val Ile Met Leu Phe Val Ser
         10                  15                  20 acc att gcc aat gtc tgg ttg gtt tcc aat acg gta gat gca tca gta    332
Thr Ile Ala Asn Val Trp Leu Val Ser Asn Thr Val Asp Ala Ser Val
             25                  30                  35 ggt ctt tgg aaa aac tgt acc aac att agc tgc agt gac agc ctg tca    380
Gly Leu Trp Lys Asn Cys Thr Asn Ile Ser Cys Ser Asp Ser Leu Ser
 40                  45                  50 tat gcc agt gaa gat gcc ctc aag aca gtg cag gcc ttc atg att ctc    428
Tyr Ala Ser Glu Asp Ala Leu Lys Thr Val Gln Ala Phe Met Ile Leu
 55                  60                  65                  70 tct atc atc ttc tgt gtc att gcc ctc ctg gtc ttc gtg ttc cag ctc    476
Ser Ile Ile Phe Cys Val Ile Ala Leu Leu Val Phe Val Phe Gln Leu
             75                  80                  85 ttc acc atg gag aag gga aac cgg ttc ttc ctc tca ggg gcc acc aca    524
Phe Thr Met Glu Lys Gly Asn Arg Phe Phe Leu Ser Gly Ala Thr Thr
                 90                  95                 100 ctg gtg tgc tgg ctg tgc att ctt gtg ggg gtg tcc atc tac act agt    572
Leu Val Cys Trp Leu Cys Ile Leu Val Gly Val Ser Ile Tyr Thr Ser
            105                 110                 115 cat tat gcg aat cgt gat gga acg cag tat cac cac ggc tat tcc tac    620
His Tyr Ala Asn Arg Asp Gly Thr Gln Tyr His His Gly Tyr Ser Tyr
        120                 125                 130 atc ctg ggc tgg atc tgc ttc tgc ttc agc ttc atc atc ggc gtt ctc    668
Ile Leu Gly Trp Ile Cys Phe Cys Phe Ser Phe Ile Ile Gly Val Leu
135                 140                 145                 150 tat ctg gtc ctg aga aag aaa taaggccgga cgagttcatg gggatctggg       719
Tyr Leu Val Leu Arg Lys Lys
                155 gggtggggag gaggaagccg ttgaatctgg gagggaagtg gaggttgctg tacaggaaaa   779 accgagatag gggaggggg aggggggaagc aaagggggga ggtcaaatcc caaaccatta   839 ctgaggggat tctctactgc caagccctg ccctgggag aaagtagttg gctagtactt    899 tgatgctccc ttgatgggt ccagagagcc tccctgcagc caccagactt ggcctccagc   959 tgttcttagt gacacacact gtctggggcc ccatcagctg ccacaacacc agccccactt  1019 ctgggtcatg cactgaggtc cacagaccta ctgcactgag ttaaaatagc ggtacaagtt  1079 ctggcaagag cagatactgt ctttgtgctg aatacgctaa gcctggaagc catcctgccc  1139 ttctgaccca agcaaaaca tcacattcca gtctgaagtg cctactgggg ggctttggcc   1199 tgtgagccat tgtccctctt tggaacagat atttagctct gtggaattca gtgacaaaat  1259 gggaggagga aagagagttt gtaaggtcat gctggtgggt tagctaaacc aagaaggaga  1319 ccttttcaca atggaaaacc tggggatgg tcagagccca gtcgagacct cacacacggc   1379 tgtccctcat ggagacctca tgccatggtc tttgctaggc ctcttgctga aagccaaggc  1439 agctcttctg gagtttctct aaagtcacta gtgaacaatt cggtggtaaa agtaccacac  1499
```

```
aaactatggg atccaagggg cagtcttgca acagtgccat gttagggtta tgttttagg      1559 attcccctca atgcagtcag tgtttctttt aagtatacaa caggagagag atggacatgg      1619
ctcattgtag cacaatccta ttactcttcc tctaacattt ttgaggaagt tttgtctaat      1679
tatcaatatt gaggatcagg gctcctaggc tcagtggtag ctctggctta gacaccacct      1739
ggagtgatca cctcttgggg accctgccta tcccacttca caggtgaggc atggcaattc      1799
tggaagctga ttaaaacaca cataaaccaa aaccaaacaa caggcccttg ggtgaaaggt      1859
gctatataat tgtgaagtat taagcctacc gtatttcagc catgataaga acagagtgcc      1919
tgcattccca ggaaaatacg aaaatcccat gagataaata aaaatatagg tgatgggcag      1979
atcttttctt taaaataaaa aagcaaaaac tcttgtggta cctagtcaga tggtagacga      2039
gctgtctgct gccgcaggag cacctctata caggacttag aagtagtatg ttattcctgg      2099
ttaagcaggc attgctttgc cctggagcag ctatttaag ccatctcaga ttctgtctaa      2159 agggttttt tggaagacg ttttctttat cgccctgaga agatctaccc caggagaat      2219 ctgagacatc ttgcctactt ttctttatta gctttctcct catccatttc ttttatacct      2279
ttcctttttg gggagttgtt atgccatgat ttttggtatt tatgtaaaag gattattact      2339
aattctattt ctctatgttt attctagtta aggaaatgtt gagggcaagc caccaaatta      2399
cctaggctga ggttagagag attggccagc aaaaactgtg ggaagatgaa ctttgtcatt      2459
atgatttcat tatcacatga ttatagaagg ctgtcttagt gcaaaaaaca tacttacatt      2519
tcagacatat ccaaagggaa tactcacatt ttgttaagaa gttgaactat gactggagta      2579
aaccatgtat tcccttatct tttactttt ttctgtgaca tttatgtctc atgtaatttg      2639
cattactctg gtggattgtt ctagtactgt attgggcttc ttcgttaata gattatttca      2699
tatactataa ttgtaaatat tttgatacaa atgtttataa ctctagggat ataaaaacag      2759
attctgattc ccttcaaaaa aaaaaaa                                           2786
```

<210> SEQ ID NO 2
<211> LENGTH: 157
<212> TYPE: PRT
<213> ORGANISM: Homo sapiens

<400> SEQUENCE: 2

Met Leu Val Leu Leu Ala Gly Ile Phe Val Val His Ile Ala Thr Val
1               5                   10                  15

Ile Met Leu Phe Val Ser Thr Ile Ala Asn Val Trp Leu Val Ser Asn
            20                  25                  30

Thr Val Asp Ala Ser Val Gly Leu Trp Lys Asn Cys Thr Asn Ile Ser
        35                  40                  45

Cys Ser Asp Ser Leu Ser Tyr Ala Ser Glu Asp Ala Leu Lys Thr Val
    50                  55                  60

Gln Ala Phe Met Ile Leu Ser Ile Ile Phe Cys Val Ile Ala Leu Leu
65                  70                  75                  80

Val Phe Val Phe Gln Leu Phe Thr Met Glu Lys Gly Asn Arg Phe Phe
                85                  90                  95

Leu Ser Gly Ala Thr Thr Leu Val Cys Trp Leu Cys Ile Leu Val Gly
            100                 105                 110

Val Ser Ile Tyr Thr Ser His Tyr Ala Asn Arg Asp Gly Thr Gln Tyr
        115                 120                 125

His His Gly Tyr Ser Tyr Ile Leu Gly Trp Ile Cys Phe Cys Phe Ser
    130                 135                 140

-continued

```
Phe Ile Ile Gly Val Leu Tyr Leu Val Leu Arg Lys Lys
145                 150                 155

<210> SEQ ID NO 3
<211> LENGTH: 2614
<212> TYPE: DNA
<213> ORGANISM: Murinae gen. sp.
<220> FEATURE:
<221> NAME/KEY: CDS
<222> LOCATION: (90)..(569)

<400> SEQUENCE: 3
gaccagcaga ctgctctacc acccagggca tctgcctctc tcactggata ctccagaatt      60
ctctactcag aagtcaccaa aaagccaag atg ttg gtg cta ctg gct ggt ctc      113
                                 Met Leu Val Leu Leu Ala Gly Leu
                                  1               5 ttt gtg gtc cac att gcc act gcc att atg ctg ttt gtc tcc acc att      161
Phe Val Val His Ile Ala Thr Ala Ile Met Leu Phe Val Ser Thr Ile
     10                  15                  20 gcc aac gtc tgg atg gtt gca gat tac gca aat gca tct gta ggg ctt      209
Ala Asn Val Trp Met Val Ala Asp Tyr Ala Asn Ala Ser Val Gly Leu
 25                  30                  35                  40 tgg aag aac tgc act ggt ggt aac tgc gac ggc tcc ctg tcc tac ggc      257
Trp Lys Asn Cys Thr Gly Gly Asn Cys Asp Gly Ser Leu Ser Tyr Gly
                 45                  50                  55 aat gaa gat gct atc aag gta gtg caa gcc ttc atg atc ctc tcc atc      305
Asn Glu Asp Ala Ile Lys Val Val Gln Ala Phe Met Ile Leu Ser Ile
             60                  65                  70 atc ttc tcc atc atc tcc ctc gtg gtc ttc gtg ttc cag ctc ttc act      353
Ile Phe Ser Ile Ile Ser Leu Val Val Phe Val Phe Gln Leu Phe Thr
         75                  80                  85 atg gag aag gga aac cgg ttc ttc ctc tcg ggg tcc acc atg ctg gtg      401
Met Glu Lys Gly Asn Arg Phe Phe Leu Ser Gly Ser Thr Met Leu Val
     90                  95                 100 tgc tgg ctg tgt atc ctg gtt gga gtg tca atc tac act cat cat tac      449
Cys Trp Leu Cys Ile Leu Val Gly Val Ser Ile Tyr Thr His His Tyr
105                 110                 115                 120 gcc cac agc gaa ggg aac ttc aac tcc agc agc cac caa ggc tat tgt      497
Ala His Ser Glu Gly Asn Phe Asn Ser Ser Ser His Gln Gly Tyr Cys
                125                 130                 135 ttc atc ctg acc tgg atc tgc ttc tgt ttc agc ttc atc atc ggc ata      545
Phe Ile Leu Thr Trp Ile Cys Phe Cys Phe Ser Phe Ile Ile Gly Ile
            140                 145                 150 ctc tat atg gtc ctg agg aag aaa taagccgaat acgctcatgg gcgtctgggg     599
Leu Tyr Met Val Leu Arg Lys Lys
        155                 160 gcggggtggg ctgggtagga ggaagcaacc taacctggga gggaagcagg agtcactgtg     659
taggaataac agagagggga ggggggtggg gagagggaag gaagaggggg agaggcccaa     719
acccaaacca tatctggggc ggtgggattc tctactgcca ggcacccatc cttggaagaa     779
agttgttggc tgatatgctg atgcttcctt gacgtcacca gagagtcctc ctctagccac     839
cgaatatggc tccgtccatc ctcaattaca tacactcggg gcctcccag ctgccatacc      899 actggcgcca ctcttgaggg tggctgctgg gtcacacact gaggtcttcc acatccatat     959
catcaagttc tgatggtggt tcaggtctta gcaagacag atattgcccg atgctgaggc     1019
taagtctgga agccactttg tccttgtgac ctaaaaccaa acatcaaatc cagatcccat     1079
gtgcctgtag tgggagcttt ggccaggaag ccaatgtgca tatttgggtg gcctttctaa     1139
caaaagtata ggatgatgag agatggtttg taagttcaag ctgatggaat tggtttagcc     1199
```

-continued

```
aagaaatgga agtttctacc ccagaggatc ttggagacag gtggggacag gcagtgctcc    1259
tcagtcacgt gtcaccgagc tgtccctcat ggaggcctcc tgttgtgaac tctgctagac    1319
tctcacttac agccaaggca gcttttctgg agttttttcta gattctctag agccaaagat   1379
gataatgcct cacaaaacat agggtcaaag catatgccca ccgcagtgct atagtaagtt    1439
tgtgggtttt taggattccc ccaaagcact caatgtatct tgtatatgta acaggggaga    1499
aatgcatgtg ttcctttgac atacaattct gaactaggaa tatttgagga agtccaatga    1559
tgaccaacaa cactggggac cgataatata acatctaaat gcagtagtca ctgttgcttt    1619
gacctgggct ggagtggtct cctctcaaca gctttcatca cactattttc cagctaaaga    1679
tggcaaagct gtaagccaat taacatatac accaacctaa actaaagaac cagtcctgag    1739
ggtgtgagca aggtgctat ctggttatgg attattaagc aaaccatatt tcatttatgt     1799
tgagaagaga atgcctgccc tcagggaaaa aaaatgtaa ttgtgtgaga tgaataaagt      1859
cctggtgata ggcagacagt ttctttttta aaacaggaga aactcttagg gcatccagac    1919
agatggtagc taaattgttg gggctgcagg ggtattcctg tataagactt agaggtagta    1979
tgatatctca gatttctgcc ttaaagggct ttcttttag aatagtttct ttttattgcc     2039
cttagaagat catttttagg aagagtatga gctatctttt ctacaattct tttcctaggg    2099
aatattctta tccatttctt aaatacaatt cttttgggag ggagttttta tgctatagtt    2159
gctggtattt atgtaaaggg acccattact aagtgtattt ctctagcata ttatgtttaa    2219
gggactgttc aaggtaggtt actgaactgc cgggctgatg ttagagacac tggccagaaa    2279
agctataata agttcttaaa ttataatttg atcactatac atttgttcta tgctgcctta    2339
tgttcataag aatatcaaca gacagctaga gccagaaaaa aatagtcaca ttttgttaaa    2399
aagttgaatt atgactggag tgaaccgtgc attcccttgc cttttacttt ttttctgtga    2459
catttacgtc tcatgtaatt tgcatcgcat tggtgggtta ttctagtact gtatttggct    2519
tcttcattaa taggatattt cacatactat aattgtaaat attttgatac aaatgtttat    2579
aactctaggg atataaaaac aaattctgat tccct                               2614
```

<210> SEQ ID NO 4
<211> LENGTH: 160
<212> TYPE: PRT
<213> ORGANISM: Murinae gen. sp.

<400> SEQUENCE: 4

```
Met Leu Val Leu Leu Ala Gly Leu Phe Val Val His Ile Ala Thr Ala
 1               5                  10                  15

Ile Met Leu Phe Val Ser Thr Ile Ala Asn Val Trp Met Val Ala Asp
            20                  25                  30

Tyr Ala Asn Ala Ser Val Gly Leu Trp Lys Asn Cys Thr Gly Gly Asn
        35                  40                  45

Cys Asp Gly Ser Leu Ser Tyr Gly Asn Glu Asp Ala Ile Lys Val Val
    50                  55                  60

Gln Ala Phe Met Ile Leu Ser Ile Ile Phe Ser Ile Ile Ser Leu Val
65                  70                  75                  80

Val Phe Val Phe Gln Leu Phe Thr Met Glu Lys Gly Asn Arg Phe Phe
                85                  90                  95

Leu Ser Gly Ser Thr Met Leu Val Cys Trp Leu Cys Ile Leu Val Gly
            100                 105                 110

Val Ser Ile Tyr Thr His His Tyr Ala His Ser Glu Gly Asn Phe Asn
```

```
                     115                 120                 125
     Ser Ser Ser His Gln Gly Tyr Cys Phe Ile Leu Thr Trp Ile Cys Phe
         130                 135                 140

Cys Phe Ser Phe Ile Ile Gly Ile Leu Tyr Met Val Leu Arg Lys Lys
     145                 150                 155                 160

<210> SEQ ID NO 5
<211> LENGTH: 756
<212> TYPE: DNA
<213> ORGANISM: Homo sapiens
<220> FEATURE:
<221> NAME/KEY: CDS
<222> LOCATION: (1)..(471)

<400> SEQUENCE: 5 atg ttg gtg cta ctg gct ggt atc tat gtg gtc cac atc gct act gtt       48
Met Leu Val Leu Leu Ala Gly Ile Tyr Val Val His Ile Ala Thr Val
  1               5                  10                  15 att atg cta ttt gtt agc acc att gcc aat gtc tgg ttg gtt tcc agt       96
Ile Met Leu Phe Val Ser Thr Ile Ala Asn Val Trp Leu Val Ser Ser
                 20                  25                  30 acg gca gat gca tca gta ggt ctt tgg aaa aac tgt tcc aac atg gag      144
Thr Ala Asp Ala Ser Val Gly Leu Trp Lys Asn Cys Ser Asn Met Glu
             35                  40                  45 tgc agt gac agc ctg tca tat gcc agt gaa gat gcc ctc aag aca gtg      192
Cys Ser Asp Ser Leu Ser Tyr Ala Ser Glu Asp Ala Leu Lys Thr Val
 50                  55                  60 cag gcc ttc atg att ctc tct atc atc ttc tgt gtc att gcc ctc ctg      240
Gln Ala Phe Met Ile Leu Ser Ile Ile Phe Cys Val Ile Ala Leu Leu
 65                  70                  75                  80 gtc ttc gcg ttc cag ctc ttc acc atg gag aag gga aac cgg ttc ttc      288
Val Phe Ala Phe Gln Leu Phe Thr Met Glu Lys Gly Asn Arg Phe Phe
                 85                  90                  95 ctc tca ggg gcc acc aca ctg gtg tgc tgg ctg tgc att ctt gtg ggg      336
Leu Ser Gly Ala Thr Thr Leu Val Cys Trp Leu Cys Ile Leu Val Gly
            100                 105                 110 gtg tcc atc tac act agt cat tat gcg aat cgt gat gga acg cag tat      384
Val Ser Ile Tyr Thr Ser His Tyr Ala Asn Arg Asp Gly Thr Gln Tyr
        115                 120                 125 cac cac ggc tat tcc tac atc ctg ggc tgg atc tgc ttc tgc ttc agc      432
His His Gly Tyr Ser Tyr Ile Leu Gly Trp Ile Cys Phe Cys Phe Ser
    130                 135                 140 ttc atc atc ggc gtt ctc tat ctg gtc ctg aga aag aaa taaggccgga       481
Phe Ile Ile Gly Val Leu Tyr Leu Val Leu Arg Lys Lys
145                 150                 155 cgagttcatg gggatctggg gggtggggag gaggaagccg ttgaatctgg gagggaagtg    541
gaggttgctg tacaggaaaa accgagatag gggagggggg aggggaagc aaagggggga     601 ggtcaaatcc caaaccatta ctgaggggat tctctactgc caagcccctg ccctggggag    661
aaagtagttg gctagtactt tgatgctccc ttgatgggt ccagagagcc tcctgcagc      721 caccagactt ggcctccagc tgttcttagt gacac                               756

<210> SEQ ID NO 6
<211> LENGTH: 157
<212> TYPE: PRT
<213> ORGANISM: Homo sapiens

<400> SEQUENCE: 6

Met Leu Val Leu Leu Ala Gly Ile Tyr Val Val His Ile Ala Thr Val
```

```
                1               5              10              15
            Ile Met Leu Phe Val Ser Thr Ile Ala Asn Val Trp Leu Val Ser Ser
                        20                  25                  30

Thr Ala Asp Ala Ser Val Gly Leu Trp Lys Asn Cys Ser Asn Met Glu
                        35                  40                  45

Cys Ser Asp Ser Leu Ser Tyr Ala Ser Glu Asp Ala Leu Lys Thr Val
                        50                  55                  60

Gln Ala Phe Met Ile Leu Ser Ile Ile Phe Cys Val Ile Ala Leu Leu
             65                 70                  75                  80

Val Phe Ala Phe Gln Leu Phe Thr Met Glu Lys Gly Asn Arg Phe Phe
                        85                  90                  95

Leu Ser Gly Ala Thr Thr Leu Val Cys Trp Leu Cys Ile Leu Val Gly
                       100                 105                 110

Val Ser Ile Tyr Thr Ser His Tyr Ala Asn Arg Asp Gly Thr Gln Tyr
                       115                 120                 125

His His Gly Tyr Ser Tyr Ile Leu Gly Trp Ile Cys Phe Cys Phe Ser
                       130                 135                 140

Phe Ile Ile Gly Val Leu Tyr Leu Val Leu Arg Lys Lys
            145                 150                 155

<210> SEQ ID NO 7
<211> LENGTH: 14
<212> TYPE: PRT
<213> ORGANISM: Artificial Sequence
<220> FEATURE:
<223> OTHER INFORMATION: Synthetic protein identified in Ruegg et al.
<300> PUBLICATION INFORMATION:
<301> AUTHORS: Ruegg, Curtis L. et al.
<302> TITLE: B4B, a  Novel Growth-Arrest Gene, is Expressed by a
      Subset of Progenitor/Pre-B Lymphocytes Negative for
      Cytoplasmic u-Chain
<303> JOURNAL: J. Immunol.
<304> VOLUME: 157
<305> ISSUE: 1
<306> PAGES: 72-80
<307> DATE: 1996

<400> SEQUENCE: 7

Cys Ser Asp Ser Leu Ser Tyr Ala Ser Glu Asp Ala Leu Lys
 1               5                  10

<210> SEQ ID NO 8
<211> LENGTH: 13
<212> TYPE: PRT
<213> ORGANISM: Artificial sequence
<220> FEATURE:
<223> OTHER INFORMATION: Synthetic protein identified in Ruegg et al.
<300> PUBLICATION INFORMATION:
<301> AUTHORS: Ruegg, Curtis L. et al.
<302> TITLE: B4B, a  Novel Growth-Arrest Gene, is Expressed by a
      Subset of Progenitor/Pre-B Lymphocytes Negative for
      Cytoplasmic u-Chain
<303> JOURNAL: J. Immunol.
<304> VOLUME: 157
<305> ISSUE: 1
<306> PAGES: 72-80
<307> DATE: 1996

<400> SEQUENCE: 8

Ser His Tyr Ala Asn Arg Asp Gly Thr Gln Tyr His His
 1               5                  10

<210> SEQ ID NO 9
<211> LENGTH: 14
<212> TYPE: PRT
```

-continued

```
<213> ORGANISM: Artificial Sequence
<220> FEATURE:
<223> OTHER INFORMATION: Synthetic protein from the first extracellular
      loop of PAP

<400> SEQUENCE: 9

Cys Ser Asp Ser Leu Ser Tyr Ala Ser Glu Asp Ala Leu Lys
 1               5                  10

<210> SEQ ID NO 10
<211> LENGTH: 11
<212> TYPE: PRT
<213> ORGANISM: Artificial Sequence
<220> FEATURE:
<223> OTHER INFORMATION: Synthetic protein from the second extracellular
      loop of PAP

<400> SEQUENCE: 10

His Tyr Ala Asn Arg Asp Gly Thr Gln Tyr His
 1               5                  10
```

BREAST CARCINOMA-ASSOCIATED GENE

This is a continuation of copending application Ser. No. 09/254,129, filed May, 12, 1999.

BACKGROUND OF THE INVENTION

The present invention concerns a pharmaceutical composition, its use in tumour diagnosis, therapy and prevention, methods for diagnosing, treating and preventing tumours as well as antibodies and their use.

The unregulated growth of tumour cells is caused by a new expression pattern of genes which regulate the cell cycle control, adhesion, angiogenesis, invasiveness and finally the formation of metastases (Pardee, Advances in Cancer Res. 65 (1994), 213–227; Ponta et al., Biochem. Biophys. Acta 1198 (1994), 1–10). The clinical course of tumour diseases such as breast cancer is characterized by several defined molecular processes such as oestrogen-independent growth, tamoxifen resistance, expression of vimentin, increase in invasiveness and finally cross-resistance towards a large number of chemotherapeutic agents which is often referred to as multi-drug resistance (cf. e.g. Clarke et al., J. Endocrinol. 122 (1989), 331–340; Sommers et al., Cancer Res. 53 (1992), 5190–5197; Sommers et al., Cancer Res. 49 (1989), 4258–4263 and Saceda et al., Mol. Endocrinol. 2 (1988), 1157–1162).

A key concern of tumour research is to identify genes which play an important role in the progression of tumour diseases and to provide new agents for tumour diagnosis, prevention or therapy on the basis of these genes.

SUMMARY OF THE INVENTION

The present invention describes the identification, cloning and characterization of the gene for a polypeptide which is named progression-associated protein "PAP". This protein is expressed in the metastasising human mammary carcinoma cell line MCF-7$_{ADR}$ whereas no expression was found in the non-metastasising mammary carcinoma cell line MCF-7. Hence the PAP protein, a nucleic acid coding therefor as well as antibodies directed against the protein are suitable as agents for the diagnosis, therapy or prevention of tumour diseases and especially of breast cancer.

The invention provides a pharmaceutical composition which is characterised in that it contains the following active components:

(A) a nucleic acid which comprises (a) the protein-coding nucleotide sequence shown in SEQ ID NO.1, (b) a nucleotide sequence corresponding to the sequence from (a) within the scope of the degeneracy of the genetic code, (c) a sequence hybridizing with the sequences from (a) or/and (b) under stringent conditions or (d) an at least 20 nucleotide long section of the sequences from (a), (b) or/and (c), (B) a polypeptide or peptide which is coded by a nucleic acid according to (A) or/and (C) an antibody to a polypeptide or peptide according to (B).

In this connection stringent hybridization conditions are understood to mean that a hybridization still occurs after washing at 55° C., preferably at 62° C., particularly preferably at 68° C. in a low salt buffer (e.g. 0.2×SSC, 0.1% SCS) (see also Sambrook et al., (1989), Molecular Cloning, A Laboratory Manual, Cold Spring Harbor Laboratory Press).

In a preferred embodiment the pharmaceutical composition additionally contains common pharmaceutical carrier substances, auxiliary substances or additives.

The protein-coding nucleotide sequence shown in SEQ ID NO. 1 codes for a protein with a length of 157 amino acids which corresponds to the B4B nucleotide sequence described by Ruegg et al., 1996 (B4B, a Novel Growth-Arrest Gene, Is Expressed by a Subset of Progenitor/Pre-B Lymphocytes Negative for Cytoplasmic µ-Chain, Am.Ass.Imm., 1995, p. 72–80) and has a homology to already known proteins. In the experiments carried out by Ruegg et al., (supra) the expression of the B4B protein is claimed to arrest the growth of Cos-7 cells. Hence the use of the B4B protein is postulated as a potential tumour suppressor.

One protein which is homologous to PAP is the rabbit protein CL-20 which is induced in vitro during the differentiation of rabbit tracheal cells and occurs most frequently in squamous epithelial tissue (Marvin, J. Biol. Chem. 270 (1995), 28910–28916). The expression of CL-20 does not depend on the growth conditions but retinoids which inhibit the differentiation of squamous epitheleum repress the induction of CL-20.

A further protein which is homologous to PAP is the rat epithelial membrane protein EMP-1 which mainly occurs in the proliferation and differentiation zones of the outer gastric gland as well as in epithelial cells of the stomach region (Taylor et al., J. Biol. Chem. 270 (1995), 28824–28833).

PAP is also homologous to the peripheral myelin protein PMP22 from man, mouse and rat which is a myelin-associated transmembrane structural protein. PMP22 is a specific protein for growth inhibition which prevents cell cycle progression (Hayasaka et al., BBRC 186 (1992), 827–831; Edomi et al., Gene 126 (1993), 289–290; Welcher et al., Proc. Natl. Acad. Sci. USA 88 (1991), 7195–7198; Spreyer et al., EMBO J. 10 (1991), 3661–3668).

On the basis of the data of Ruegg et al. and the homology to the PMP22 protein responsible for maintaining the cellular dormant state, it was extremely surprising that the PAP protein is selectively expressed in the strongly degenerate metastisising cell line MCF-7$_{ADR}$ but not in the less degenerate cell line MCF-7.

Furthermore PAP has a high degree of homology to previously not yet published proteins whose sequences are stored in the gene library. These proteins are referred to as murine TMP or human TMP and have an amino acid identity of 76% or 95% to PAP.

The nucleotide and amino acid sequences of murine TMP are shown in SEQ ID NO. 3 and 4 and of human TMP are shown in SEQ ID NO.5 and 6. PAP and human TMP mainly differ in the region of the amino acids 32–48.

A further subject matter of the present invention is the use of a vector which contains at least one copy of a nucleic acid as previously defined or a section thereof for the transformation of a cell. This nucleic acid can for example be genomic DNA, cDNA or mRNA. It is preferably a recombinant DNA molecule.

The invention also concerns the use of a vector which contains an at least 20 nucleotide long section of the protein-coding sequence shown in SEQ ID NO.1. This section preferably contains a nucleotide sequence specific for PAP. These nucleic acids are especially suitable for preparing antisense nucleic acids that can be used therapeutically which preferably have a length of up to 50 nucleotides.

The vector containing the nucleic acid can be capable of replication in eukaryotes or prokaryotes. It can be a vector that can be integrated into the genome of the host cell e.g. bacteriophage λ, or it can be a vector that is present extrachromosomally (e.g. a plasmid). The vector according to the invention can be obtained by subcloning the PAP-DNA into a base vector. Such base vectors and in particular vectors containing the elements necessary for protein expression are familiar to a person skilled in the art.

When cloning a nucleic acid coding for PAP, it is possible to prepare an expression vector that can be expressed in a suitable host cell to form the protein according to the invention. Preferred host cells are microorganisms such as E. coli or yeast and also higher cells such as mammalian or insect cells. Preferred expression vectors are for example plasmids, bacteriophage λ for prokaryotes, yeast vectors or viral vectors for higher cells e.g. SV40, vaccinia, baculovirus. With regard to the expression of a PAP-coding nucleic acid reference is made in particular to the methods stated in Sambrook et al. (supra).

Systems suitable for expressing PAP contain suitable vectors e.g. the vector pcDNA1 (Invitrogen) in which the DNA to be expressed is under the control of the cytomegalovirus promoter.

A further subject matter of the present invention is a cell which is characterized in that it is transformed with a nucleic acid which comprises
(a) the protein coding nucleotide sequence shown in SEQ ID NO.1,
(b) a nucleotide sequence corresponding to the sequence from (a) within the scope of the degeneracy of the genetic code or
(c) a nucleotide sequence which has a homology of more than 95% to a sequence from (a) or/and (b) provided that the cell is not a Cos-7 cell.

The cell can be a eukaryotic as well as a prokaryotic cell. Methods for transforming cells with nucleic acids are part of the general state of the art and do not therefore need to be elucidated in more detail.

A further subject matter of the present invention is the use of a PAP polypeptide with the amino acid sequence shown in SEQ ID NO. 2, fragments of this polypeptide or variants thereof as an immunogen for producing antibodies.

Variants are understood as sequences which differ from the amino acid sequence shown in SEQ ID NO. 2 by substitution, deletion or/and insertion of individual amino acids or short amino acid sections.

The term "variant" includes naturally occurring allelic variations of PAP as well as protein produced by recombinant DNA technology (in particular produced by in vitro mutagenesis with the aid of chemically-synthesized oligonucleotides) whose biological or/and immunological activity essentially corresponds to that of the protein shown in SEQ ID NO.2.

In a preferred embodiment the invention concerns the use of the pharmaceutical composition for tumour diagnosis and in particular for the diagnosis of mammary carcinomas. Furthermore an application as a tumour progression marker whose expression correlates with the progress of the tumour or/and with the degree of metastasis is especially preferred.

In a particularly preferred embodiment for the diagnosis of tumours the expression rate of the PAP protein correlates with the tumour stage and in particular with the tendency to form metastases.

A preferred embodiment is the use of the pharmaceutical composition for tumour therapy or prevention and an application for the therapeutic or preventive treatment of mammary carcinomas is particularly preferred.

Yet a further subject matter of the present invention is a method for diagnosing tumours in which a patient or a tissue derived from a patient is brought into contact with a pharmaceutical composition according to the invention and the expression of the PAP protein is determined qualitatively or/and quantitatively. This determination can for example be carried out at the nucleic acid level by using nucleic acid hybridization probes or by reverse transcription/PCR at the protein level by using antibodies in cytochemical or histochemical methods. The pharmaceutical composition is particularly preferably used as a tumour progression marker to identify the aggressiveness of tumours and especially of mammary carcinomas by quantifying the PAP expression for example after an operative procedure or to monitor the progress of a chemotherapeutic treatment.

Finally the present invention also concerns a method for the treatment or prevention of tumours in which a pharmaceutical composition according to the invention is administered to a patient which contains the active component in an amount that is effective against tumours. Specific examples of pharmaceutical compositions which are suitable for therapeutic purposes are for example bispecific antibodies and antibody-toxin or antibody-enzyme conjugates such as those used in the clinical studies for the HER-2 gene (cf. in this connection Weiner et al., Cancer Res. 55 (1995), 4586–4593; Weiner et al., J. Hematotherapy 4 (1995), 453–456; Repp et al., J. Hematotherapy 4 (1995), 415–421; Valone, J. Hematotherapy 4 (1995), 471–475; Rodrigues, Cancer Res. 55 (1995), 63–70).

A further subject matter of the invention is a method for treating tumours which is characterized in that the expression of the PAP protein in the tumour cells is reduced or eliminated.

The expression can be reduced by using agents or methods which interfere with transcription or/and translation or reduce the half-life of the mRNA.

For example anti-sense oligonucleotides to the nucleotide sequence shown in SEQ ID NO.1 can be introduced into the cells or the cell is transformed with an expression vector which expresses an anti-sense sequence to SEQ ID NO.1. Furthermore factors which interfere with the PAP mRNA expression or the PAP translation can be used.

The PAP expression can be completely switched off by using a so-called targeting vector for the PAP gene and carrying out a homologous recombination. The said methods are known to a person skilled in the art and therefore do not require further elucidation.

On the other hand it may be necessary for various purposes to increase the proliferation of cells if, for example, certain cell populations or subpopulations are required in large amounts or if it is intended to specifically stimulate the proliferation of certain cells in a tissue.

A further subject matter of the invention concerns a method for increasing the proliferation of a cell which is characterized in that
(A) a polypeptide or peptide is expressed in the cell or its expression is increased in the cell which is coded by
   (a) a nucleotide sequence shown in SEQ ID NO.1,
   (b) a nucleotide sequence corresponding to the nucleotide sequence from (a) within the scope of the degeneracy of the genetic code,
   (c) a nucleotide sequence which has a homology of more than 95% to a nucleotide sequence from (a) or/and (b) or
   (d) an at least 20 nucleotide long section of the sequences from (a), (b) or/and (c) or
(B) a polypeptide or peptide which is coded by a nucleic acid according to (A) is Introduced into the cell.

In addition to nucleic acids and polypeptides of PAP, antibodies to polypeptides or fragments thereof are also suitable as components of the pharmaceutical composition.

Polyclonal antibodies to a polypeptide as described above are particularly preferred provided that the antibodies are not directed towards the peptide sequence CSDSLSYASED-ALK (SEQ ID NO. 7) or SHYANRDGTQYHH (SEQ ID NO. 8) or a monoclonal antibody to a polypeptide as described above is particularly preferred. An antibody is most preferred which is characterized in that it is directed towards a peptide sequence which corresponds to the amino acids 32 to 48, 49 to 62 or 119 to 129 of the amino acid sequence shown in SEQ ID NO.2.

In this connection antibodies can be produced in the usual manner by immunizing experimental animals with the complete PAP protein or fragments thereof and subsequently isolating the resulting polyclonal antisera. Monoclonal antibodies can be obtained in a known manner from the antibody-producing cells of the experimental animals by cell fusion according to the method of Köhler and Milstein or further developments thereof. It is also possible to produce human monoclonal antibodies by known methods.

Figure 2:
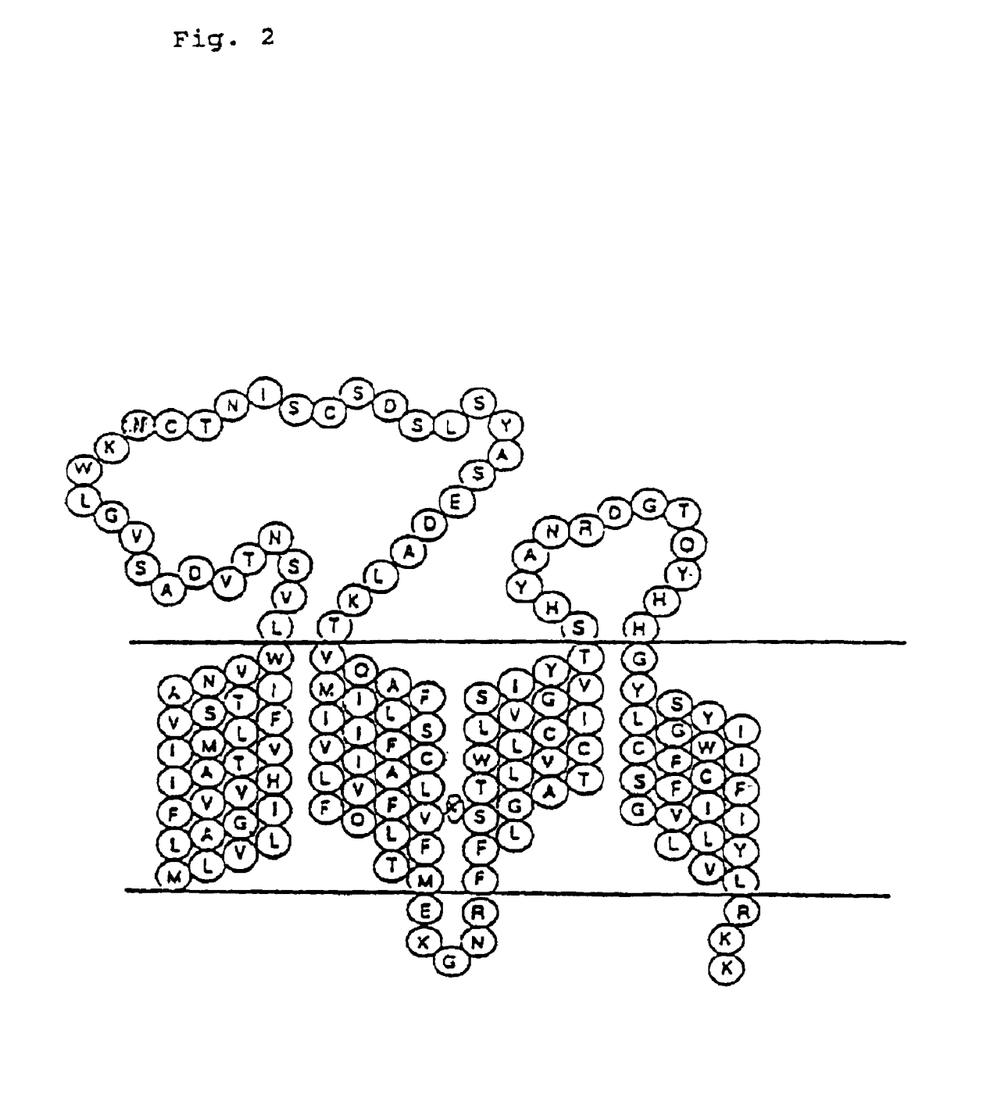
FIG. 2 shows a prediction of the topology of PAP in a lipid double layer. The filled circle represents a potential N-glycosilation site.

Peptides are preferred as the immunogen which are derived from the extracellular domains of PAP (cf. FIG. 2). Particularly preferred peptides are derived from regions which correspond to the amino acids 32–48, 49–62 or 119–129 of SEQ ID NO.2. These peptides are preferably coupled by known methods to a carrier e.g. keyhole limpet hemocyanin (Snipes et al., J. Cell. Biol. 117 (1992), 225–238). The resulting conjugates are used to immunize experimental animals e.g. rabbits.

Hence a further subject matter of the present invention is an antibody to the PAP protein or a variant thereof, preferably an antibody that exhibits no cross-reaction with homologous proteins such as EMP-1, PMP22 and CL-20. The antibody is particularly preferably directed towards a peptide sequence which corresponds to the amino acids 32 to 48, 49 to 62 or 119 to 129 of the amino acid sequence shown in SEQ ID NO.2.

A further subject matter of the invention is the use of the antibodies described above in an immunological method such as an immunoprecipitation, a Western blot, a competitive immunotest or a sandwich test.

Yet a further subject matter of the invention concerns the use of a polypeptide or a fragment thereof which is coded by (a) the protein-coding nucleotide sequence shown in SEQ ID NO.1, (b) a nucleotide sequence corresponding to the sequence from (a) within the scope of the degeneracy of the genetic code or (c) a nucleotide sequence with a homology of more than 95% to a sequence from (a) or/and (b) to produce an antibody using a phage-display antibody library.

This method enables the identification and production of an antibody to the PAP protein only using methods of recombinant DNA technology without having to use animals or (primary) cells isolated from animals.

The method therefore does not require the tedious and time-consuming steps of a classical antibody production such as immunization of experimental animals, boosting or cell fusion and selection cycles for individual clones.

The provision of a pharmaceutical composition according to the invention, of PAP protein, of a nucleic acid coding therefor and of an antibody directed towards this protein are the prerequisites for a specific search for effectors of this protein. The target for these substances should be the potential extracellular domains of the protein which are located in the region of the amino acid residues 29 to 63 and 118 to 130 of the amino acid sequence shown in SEQ ID NO.2. Substances which inhibit or activate this region of the protein are able to selectively influence PAP-controlled cell functions. Hence they can be used to treat corresponding clinical pictures. In the case of clinical pictures which are due to a deficiency of PAP it would be possible to carry out a gene therapy comprising the transfer of a nucleic acid coding for PAP by means of vectors, e.g. viral vectors, into the appropriate target tissue. On the other hand in the case of clinical pictures which are due to an uncontrolled expression of PAP, a gene therapy can be carried out which leads to an inhibition of this expression.

Moreover, the results that have been presented also provide the basis for a specific diagnosis of diseases which are causally linked to changes in PAP activity. These investigations can be carried out with the aid of specific nucleic acid probes for the detection at the nucleic acid level i.e. at the gene or transcript level or with the aid of antibodies to PAP for detection at the protein level.

The invention is further elucidated by the following examples, figures and sequence protocols.

SEQ ID NO.1 shows a nucleic acid sequence which contains the genetic information coding for PAP.

SEQ ID NO.2 shows the amino acid sequence of PAP.

SEQ ID NO.3 shows the nucleic acid sequence of mouse TMP cDNA.

SEQ ID NO.4 shows the amino acid sequence of mouse TMP.

SEQ ID NO.5 shows the nucleic acid sequence of human TMP cDNA.

SEQ ID NO.6 shows the amino acid sequence of human TMP.

DETAILED DESCRIPTION OF THE INVENTION

EXAMPLES

Example 1

Culturing Cell Lines

The cell lines MCF-7 and MCF-7$_{ADR}$ are human mammary carcinoma cell lines (Thompson et al., J. Cell. Physiol. 150 (1992), 534–544 and Fairchild et al., Cancer Res. 47 (1987), 5141–5148).

The cell line MCF-7 is non-metastasising, expresses the oestrogen receptor, exhibits oestrogen-dependent growth in the naked mouse and no expression of vimentin. The cell line MCF-7$_{ADR}$ is derived from MCF-7 and was selected via its resistance to adriamycin. It is metastasising, exhibits a multi-drug resistance, no expression of the oestrogen receptor and oestrogen-independent growth in the naked mouse.

These cell lines were cultured in improved minimal essential medium (IMEM; Gibco, Grand Island, N.Y.) containing 5% foetal bovine serum (Gibco). The cells were cultured at 37° C. and in a 5% $CO_2$ atmosphere.

Example 2

Differential Display PCR

The differential display polymerase chain reaction (DD-PCR) was carried out according to known methods (cf.

Liang and Pardee, Science 275 (1992), 967–970; Liang et al., Cancer Res. 52 (1992), 6966–6968 and Liang et al., Nucleic Acids Res. 21 (1993), 3269–3275) using the RNA-map kit (GenHunter Corp., Brookline, Mass.) according to the manufacturer's instructions.

Total RNA was isolated from MCF-7 and MCF-7$_{ADR}$ cells by the method of Chomczynski and Sacchi (Anal. Biochem. 162 (1987), 156–159) using the total RNA isolation system (Promega Corp., Madison, Wis.). DNA contaminants were removed from the RNA samples by incubation with RNase-free DNase I using the message clean kit (GenHunter Corp., Brookline, Mass.) by incubating for 30 min at 37° C.

DNA-free total RNA (0.2 μg) from MCF-7 and MCF-7$_{ADR}$ cells was used as a template for the cDNA first strand synthesis in the presence of 10 μM of the anchor primers T$_{12}$MG, T$_{12}$MC, T$_{12}$MA and T$_{12}$MT (in which M is triple degenerated for G, A and C), 1×reverse transcriptase buffer (125 mM Tris-Cl, pH 8.3; 188 mM KCl; 7.5 mM MgCL$_2$; 25 mM dithiothreitol) and 250 μM dNTP mixture. The solution was heated for 5 min to 65° C., cooled for 10 min to 37° C. and then 200 U Moloney murine leukaemia virus (MMLV) reverse transcriptase was added. After incubating for 1 hour at 37° C. the reaction was stopped by incubating for 5 minutes at 95° C.

The PCR was carried out in a reaction solution which contained 0.1 volumes of the reaction mixture for reverse transcription, 10 μM of the respective T$_{12}$MN anchor primers, 2 μM 10-mer primer with arbitrarily determined sequence, 1×PCR buffer (100 mM Tris-Cl, pH 8.4; 500 mM KCl; 15 mM MgCl$_2$; 0.01% gelatin), 25 μM dNTP, 10 μCi [α-35S] dATP and 10 U Amplitaq DNA polymerase (Perkin Elmer, Morwalk, Conn.). The PCR was carried out for a total of 40 cycles comprising 94° C. for 30 s, 40° C. for 2 min, 72° C. for 30 s and finally 5 min at 72° C.

After adding loading buffer to 3.5 μl sample in each case, the PCR products were heated for 2 min at 80° C. and then applied to a denaturing 5% polyacrylamide sequencing gel for electrophoresis. The dried gel was analysed by autoradiography for differentially expressed genes.

The bands identified in two independent DD-PCR reactions which correspond to differentially expressed genes were cut out of the dried gel. The cDNA was eluted from the gel by soaking the gel piece in 100 μM H$_2$O for 10 min and subsequently boiling for 15 min. The cDNA was isolated by ethanol precipitation in the presence of 3 M sodium acetate and 50 μg glycogen as a carrier and taken up in 10 μl H$_2$O. 4 μl of the eluted cDNA was reamplified in a second PCR. In this case the same 5' and 3' primers and the conditions described above were used except that DNTP concentrations of 20 μM were used and the reaction mixture contained no radioisotopes.

The amplified PCR fragments obtained in this manner were separated by a 1.5% agarose gel, purified and used as probes for the Northern analysis of RNA from MCF-7 and MCF-7$_{ADR}$.

Example 3

Northern Analysis

PolyA+RNA was isolated from total RNA using the polyA T-tractIII mRNA isolation system (Promega Corp., Madison, Wis.). Parallel lanes of PolyA+RNA from MCF-7 and MCF-7$_{ADR}$ cells (1 μg from each cell line) were separated according to size on a denaturing 1% agarose formaldehyde gel and then transferred onto a positively-charged nylon membrane (Boehringer Mannheim GmbH, Mannheim) by capillary blotting in 20×SSC. After UV cross-linking (Stratagene UV Stratalinker 1800), the membranes were hybridized with [α-$^{32}$P] dCTP-labelled DD-PCR products which had been prepared by the random-primed DNA labelling method and labelled up to a specific activity of 2×10$^8$ dpm/μg using the Rediprime DNA labelling system (Amersham, Braunschweig). The prehybridization (5 h) and hybridization (overnight) with radioactive probes was carried out in 50% formamide, 5% SSC, 5×Denhardt solution, 1% SDS and 100 μg/ml denaturing salmon sperm DNA at 42° C. The membranes were washed twice at room temperature for 15 min with 1×SSC, 0.1% SDS followed by washing with 0.25×SSC, 0.1% SDS at 55–60° C. for 15 min to 30 min. The membranes were then examined by autoradiography.

Those DD-PCR products in which a differential mRNA expression was detected were subcloned by the TA cloning system (Invitrogen, San Diego, Calif.) into the PCR II vector. The subcloned fragments were isolated using the Quiagen plasmid kit (Quiagen, Hilden) and again used as probes for the Northern analysis to verify the differential mRNA expression.

Example 4

Characterization of DD-PCR Fragments Which Correspond to Differentially Expressed mRNAs The subcloned fragments which were derived from differentially expressed mRNAs were sequenced in the TA cloning vector using the Dye Terminator Cycle sequencing kit (Applied Biosystems GmbH, Foster City, Calif.). The nucleotide sequence data were analysed for homology with known genes in the gene bank and EMBL databases using the computer program BLAST.

In this manner it was possible to identify one new mRNA in addition to the 10 known mRNA species which is differentially expressed in the cell line MCF-7$_{ADR}$.

In order to obtain the complete cDNA of this new mRNA, a 556 bp long subcloned DD-PCR fragment was used to screen a human heart cDNA bank (Clontech, Palo Alto, Calif.) which had been prepared in a lambda gt10 vector. In this manner an approximately 2 kb cDNA clone was isolated both strands of which were sequenced and compared with the cloned DD-PCR fragment.

In order to identify the 5' region of the cDNA, a RACE (rapid amplification of cDNA ends) PCR was carried out according to the method described by Frohmann (PCR-Meth. Appl. 4 (1994), 40–58) and Schaefer (Anal. Biochem. 227 (1995), 255–273) using the modifications of Kato et al., (Gene 150 (1994), 243–250). The 1 kb long 5' RACE PCR product obtained in this manner was sequenced and compared with the cDNA clone obtained from the screening of the cDNA bank.

The resulting nucleotide sequence of the complete cDNA was compared with known DNA sequences from the gene bank and the EMBL database.

As determined by Northern blot analysis, the newly identified mRNA is exclusively expressed in the cell line MCF-7$_{ADR}$. Hence the cDNA and the protein which it encodes was named progression-associated protein (PAP). The nucleotide and amino acid sequences of PAP are shown in SEQ ID NO.1 and 2. The nucleotide sequence comprises 2786 nt with an open reading frame of 471 nt (157 amino acids) which begins with an ATG initiation codon at position 219 and ends with the TAA stop codon at position 692. A potential N-glycosilation signal in the region of amino acids 43–45 was identified together with the amino acid 43 as a possible acceptor of the sugar group. A potential acylation site by covalent addition of myristate was identified at amino acid position 39. A possible phosphorylation site for the serine-threonine kinase casein kinase II was identified at position 48.

Figure 1:
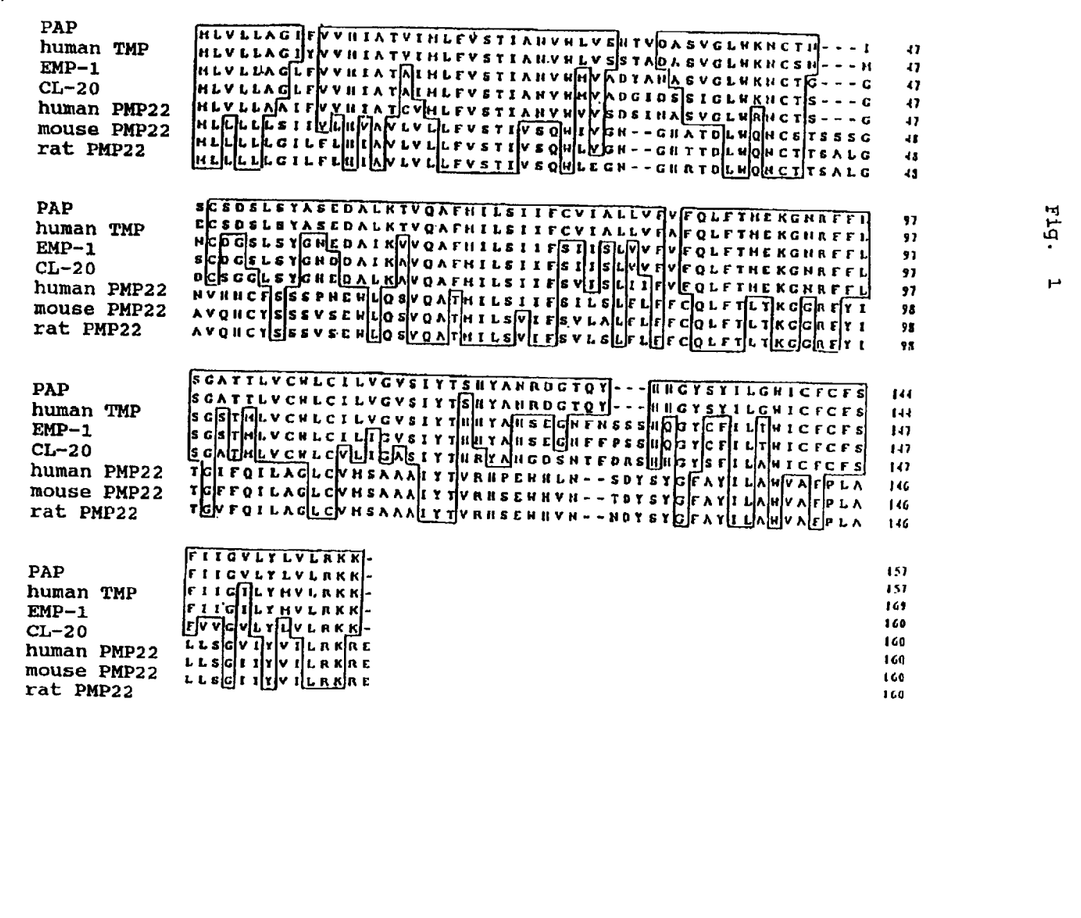
FIG. 1 shows a comparison between the amino acid sequences of human PAP (1), human TMP (2), rat EMP-1 (3), rabbit CL-20 (4), human (5), mouse (6) and rat (7) PMP 22.

The PAP cDNA is a member of a gene family. A comparison of the amino acid sequences of members of this gene family is shown in FIG. 1. Human PAP has the greatest similarity to the rabbit protein CL-20 and to the rat protein EMP-1 (identity of 77 and 76% respectively) followed by the protein PMP-22 from man, mouse and rat (identity of 41%, 43% and 41%)

Furthermore it was found that PAP is very similar to previously unpublished proteins which are referred to as murine tumour-associated membrane protein (mouse TMP, gene bank U25633, SEQ ID NO. 3/4) and human tumour-associated membrane protein (gene bank U43916, SEQ ID NO.5/6). Murine TMP has a length of 160 amino acids of which 39 amino acids are different to PAP (identity of 76%). Human TMP has a length of 157 amino acids of which 7 amino acids are different from PAP (identity of 95%)

Based on computer-assisted hydrophobicity plots and predictions of the secondary structure, it is possible to propose a model for the hypothetical topology of PAP (FIG. 2). Accordingly PAP contains 4 hydrophobic potential transmembrane domains and 2 potential extracellular domains (amino acids 29–63 and 118–130).

The greatest differences between PAP and human TMP (5 amino acids) are located in the region of the first extracellular domain in particular in the region of the amino acids 32–48.

Example 5

Expression Pattern of PAP

In order to examine the tissue-specific expression of PAP, the distribution of PAP-mRNA in various human tissues was analysed by Northern blot analysis using multiple tissue Northern blots (Clontech, Palo Alto, Calif.).

In this case it was found that PAP-mRNA is expressed in most human tissues. However, PAP-mRNA is absent in peripheral blood leukocytes and is only weakly expressed in the brain. Furthermore PAP-mRNA is absent in various leukaemia and lymphoma cell lines such as HL 60 (promyelocytic leukaemia), K562 (chronic myeloid leukaemia), Molt-4 (lymphoblastoid leukaemia), Raji (Burkitt's lymphoma) and HeLa (cervical carcinoma). However, a strong expression of PAP-mRNA was found in SW480 cells (colorectal adenocarcinoma) and in G361 melanoma cells.

Example 6

Preparation of a PAP Expression Construct and Transient Expression in COS Cells The PAP-cDNA was subcloned into the EcoRV site of the expression vector pcDNA1 (Invitrogen, San Diego, Calif.) downstream of the cytomegalovirus promoter. The original vector without a cDNA insertion was used as a negative control. Recombinant DNA was purified by means of a Quiagen column (Quiagen, Hilton, GER) and quantified by determining the absorbance at 260 nm.

COS cells which grew exponentially in DMEM containing 10% foetal calf serum were treated with trypsin, washed with phosphate-buffered saline and centrifuged at 800 g. $1.5 \times 10^6$ cells were resuspended in 200 µl phosphate-buffered saline containing 5 µg vector DNA. The cells were cooled for 5 min on ice, transferred to an electro-poration cuvette (Biorad, Herkules, Calif.) with a gap of 4 mm and subjected to an electroporation at 300 V and 125 microfarad.

The transfected cells were cooled for 5 min on ice and divided into seven 35 mm culture dishes containing 2 ml DMEM and 10% foetal calf serum and cultured for 48 h. Then the cells were washed with Tris-buffered saline, fixed for 30 min in DMEM containing 2% paraformaldehyde, washed with Tris-buffered saline and permeabilized for 30 min in Tris-buffered saline solution containing 0.1% saponin. Unspecific binding sites were blocked for 30 min at room temperature in Tris-buffered saline solution, 2% bovine serum albumin, 1% porcine skin gelatin (type A sigma), 2% goat serum and 0.1% saponin. The cells were incubated overnight at 4° C. with anti-PAP antibodies (example 7) diluted 1:500 in blocking buffer containing 0.02% saponin. Then fluorescein isothiocyanate-labelled goat anti-rabbit immunoglobulin diluted 1:200 in blocking buffer containing 0.02% saponin was added. After washing with Tris-buffer saline solution the cells were mounted on slides and the immunoreactivity was visualized by confocal microscopy using a Biorad MRC-600 scanner together with a Zeiss Axiophot fluorescence microscope. Preimmune serum (1:500) s primary antiserum was used as a negative control.

Example 7

Antibody Production

Anti-peptide antibodies were produced against synthetic peptides from the first and second extracellular loops of PAP.

Peptide 1: $Cys^{49}$-Ser-Asp-Ser-Leu-Ser-Tyr-Ala-Ser-Glu-Asp-Ala-Leu-$Lys^{62}$—COOH (SEQ ID 9).

Peptide 2: $His^{119}$-Tyr-Ala-Asn-Arg-Asp-Gly-Thr-Gln-Tyr-$His^{129}$—COOH (SEQ ID 10).

The peptides were coupled to keyhole limpet hemocyanin by known methods (Snipes et al., (1992), supra). The conjugates were used to immunize rabbits with complete Freund's adjuvant. Subsequently the immunization was boosted at two-week intervals for a total of 4 times using 500 µg peptide and incomplete Freund's adjuvant. Blood was withdrawn from the immunized animals and the serum was isolated. The activity of the immunoserum was tested by a solid phase ELISA (example 6).

---

What is claimed is:

1. A process for detecting the presence or absence, in a mammary tumor, of the mRNA encoded by the nucleic acid sequence shown in ID NO: 1, comprising:

(a) obtaining from a patient a cell containing mRNA from the mammary tumor;

(b) contacting the mRNA with an oligonucleotide consisting of a nucleic acid sequence of SEQ ID NO: 1 or a nucleic acid sequence, though not identical to SEQ ID NO: 1, due to the degeneracy of the genetic code encodes a polypeptide having the amino acid sequence of the polypeptide encoded by SEQ ID NO:1; and (c) detecting the presence or absence of hybridization of the mRNA from the cell to the oligonucleotide of step(b)

wherein the presence of hybridization indicates the presence of a PAP mRNA in the cell and that the cell has the tendency to form metastases.

2. The process of claim 1, wherein the nucleic acid sequence of the oligonucleotide is complementary to the nucleic acid sequence shown in SEQ ID NO:1.

* * * * *